United States Patent [19]

Berryessa

[11] Patent Number: 4,531,935
[45] Date of Patent: Jul. 30, 1985

[54] CARDIOPLEGIA/AIR ASPIRATION CANNULA

[75] Inventor: Richard Berryessa, Salt Lake City, Utah

[73] Assignee: Med-West, Incorporated, Salt Lake City, Utah

[21] Appl. No.: 457,693

[22] Filed: Jan. 13, 1983

[51] Int. Cl.³ .................... A61M 5/14; A61M 25/00
[52] U.S. Cl. ........................... 604/45; 604/44; 604/53; 604/164
[58] Field of Search ............... 604/4, 27, 43–45, 604/53, 164–170

[56] References Cited

U.S. PATENT DOCUMENTS

| | | | |
|---|---|---|---|
| 3,507,281 | 4/1970 | Cassou | 604/232 |
| 4,073,297 | 2/1978 | Kopp | 604/44 |
| 4,270,535 | 6/1981 | Bogue et al. | 604/44 |
| 4,299,217 | 11/1981 | Sagae et al. | 604/44 |
| 4,416,280 | 11/1983 | Carpenter et al. | 604/4 |
| 4,445,884 | 5/1984 | Kurtz et al. | 604/4 |

Primary Examiner—C. Fred Rosenbaum
Assistant Examiner—Michelle Lester
Attorney, Agent, or Firm—Workman, Nydegger & Jensen

[57] ABSTRACT

A cardioplegia/air aspiration cannula assembly for delivering cardioplegic fluid to and for aspirating air from the aorta during surgery. The assembly includes a hub having a single needle portion. The needle portion has an inner cannula which extends through the hub and defines an inner lumen through which the cardioplegic fluid is injected. An outer cannula is coaxially positioned over the inner cannula and is diametrally spaced therefrom to define an outer lumen. A plurality of holes are formed in the sides of the outer cannula through which air can be aspirated. The outer lumen defined by the space between the inner and outer cannulae is in fluid communication with a passageway passing through a side branch of the hub which can be connected to a vacuum source.

13 Claims, 6 Drawing Figures

CARDIOPLEGIA/AIR ASPIRATION CANNULA

BACKGROUND

1. Field of the Invention

The present invention relates to cannulae used during cardiac surgery and, more particularly, to a double lumen cannula for both delivering cardioplegic fluid to and for aspirating air from the aorta.

2. The Prior Art

Since the early days of cardiac surgery it has been recognized that in order to provide the optimum surgical conditions when operating in or upon the heart, it is necessary to interrupt the normal operation of the heart since it is very difficult to operate while the heart is beating and while blood is flowing through it. Thus, in order to be able to efficiently perform cardiac surgery it is sometimes necessary to use cardiopulmonary-bypass techniques and to isolate the heart from its life-giving blood supply.

It has been found that most deaths occurring after cardiac surgery are due to acute cardiac failure. At first it was believed that the heart was simply beyond repair and that the operation had failed to correct the problem. Later, however, it was discovered that many of these postoperative deaths were due in part to myocardial injury occurring as a direct result of the surgery. A considerable amount of research has been performed to determine the exact cause of these myocardial injuries and the optimum procedures for maintaining myocardial integrity during open heart surgery.

One of the first methods utilized to protect the myocardium during surgery was normothermic perfusion of the empty beating heart. This method was utilized in an effort to maintain the heart, as near as possible, in normal conditions during the surgery. Although this procedure eliminated the problem of blood flow, disection and suturing were still difficult to perform because of the firmness of the myocardium and the beating of the heart. Additionally, it was found that a significant amount of damage still occurred to the myocardium when this procedure was utilized.

A second method which was developed to protect the myocardium was intermittent cardiac ischemia with moderate cardiac hypothermia. This method requires that the entire body be perfused at a temperature of from 28° C. to 32° C., thus slowing all bodily functions, including those of the heart. The heart is fibrillated before aortic cross-clamping to stop the beating. The surgeon can then operate for approximately 15-25 minutes at which time the heart beat needs to be resumed for three to five minutes. This procedure proved to be an inefficient method for performing operations and had many attendant dangers, including the fibrillation of the heart.

A third method which has been utilized is profound hypothermic cardiac ischemia. This method requires that the temperature of the heart be lowered to about 22° C. by the infusion of cooled perfusate and/or by filling the pericardium with a cold saline solution. One of the major disadvantages of this technique is that the heart continues fibrilate, exhasting the stores of substrate, becomes acidotic and with time causes irreversible muscle damage.

A fourth method which has been developed to maintain the myocardium is the infusion of cold cardioplegic fluid to cool and stop the beating of the heart. After the initial infusion, the heart is reperfused approximately every thirty minutes to maintain the cool, dormant state of the heart.

The use of cardioplegic fluids to protect the myocardium has proven to be the most advantageous method of those tested to date. However, there are still many problems which need to be overcome. For example, the injection of cardioplegic fluids into the heart creates an opportunity for air to enter the aorta and subsequently the arteries. Air embolisms can cause severe damage if they are allowed to pass through the arteries to the heart or the brain. Accordingly, it is important that steps be taken to insure that any entrapped air is removed from the aorta.

In the past, this has been accomplished by forming a small incision in the aorta and by inserting a sucker tube connected to a vacuum source. The incision in the aorta through which the sucker tube passes is in addition to the puncture which is necessary for the needle which injects the cardioplegic solution. Accordingly, in the prior art systems it has been necessary to form both an incision and a puncture wound, thus increasing the trauma to the aorta, the amount of time necessary to position the equipment, and the necessity of closing two wounds when the operation is complete.

Accordingly, if the use of cardioplegic fluids is to be the preferred method of maintaining myocardial integrity during open heart surgery, what is needed in the art is a device for the injection of cardioplegic fluids which overcomes these disadvantages.

OBJECTS AND BRIEF SUMMARY OF THE INVENTION

It is a primary object of this invention to provide a single device which can be used for both delivery of cardioplegic fluids and aspiration of air during open heart surgery.

It is a further object of this invention to provide a device which only necessitates formation of one puncture wound in the aorta to allow for infusion of cardioplegic fluids and aspiration of air.

It is another object of this invention to provide a combination cardioplegia injection and air aspiration device which is inexpensive to manufacture and is easy to handle.

These and other objects and features of the present invention will become more fully apparent from the following description and appended claims taken in conjunction with the accompanying drawings.

In accordance with the foregoing objects, the present invention provides a cardioplegia/air aspiration cannula which is used during open heart surgery for both infusion of cardioplegic fluids and aspiration of air entrapped in the aorta. The device comprises an interior cannula for delivering cardioplegic fluids and a concentric, diametrically spaced exterior cannula for aspirating air. The exterior cannula has a series of spirally positioned openings through which air is aspirated. The cannulae are concentrically mounted in a hub having fittings to connect the device to tubing leading to a vacuum source and to a source of cardioplegic fluid.

BRIEF DESCRIPTION OF THE DRAWINGS

Reference is next made to the drawings in which like parts are designated with like numerals throughout, and in which.

DETAILED DESCRIPTION OF THE PREFERRED EMBODIMENTS

Figure 1:
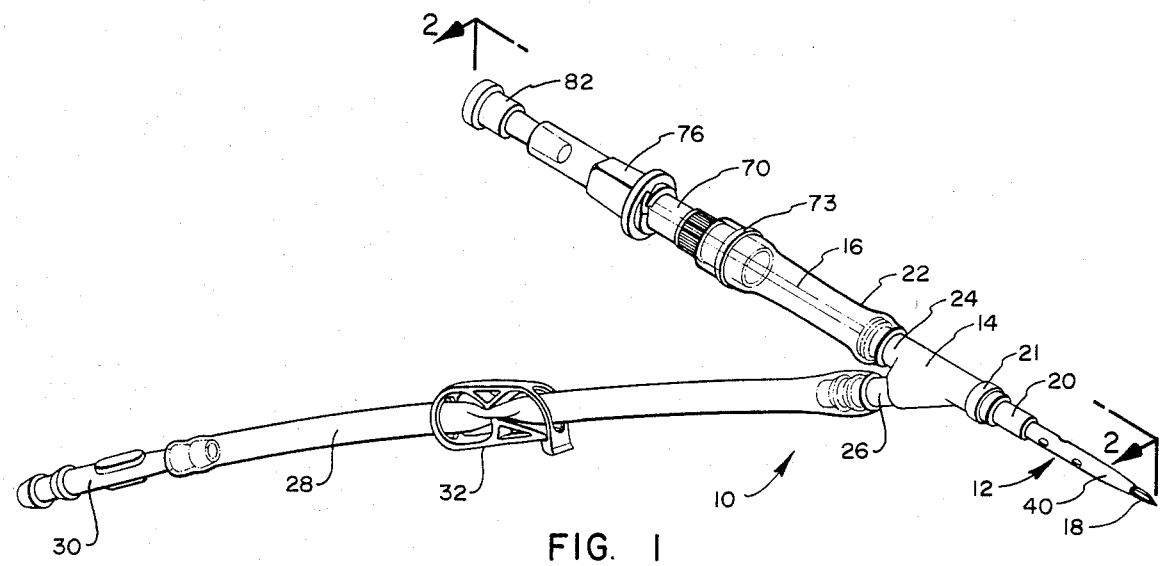
FIG. 1 is a perspective view of one presently preferred embodiment of the cardioplegia/air aspiration cannula of the present invention.

In FIG. 1, the cardioplegia/air aspiration cannula assembly of the present invention is generally designated at 10. The cannula assembly has a single needle portion, generally designated at 12, which is inserted into the aorta at the start of the surgical procedure. As hereinafter more fully described, needle portion 12 is a double lumen cannula with the interior lumen designed for injection of the cardioplegic fluid and the outer lumen designed to aspirate any air which may become entrapped in the aorta.

The outer cannula 40 of needle portion 12 is anchored in the forward end 20 of Y-shaped hub 14, which is formed of a medical-grade plastic. One branch 24 of hub 14 is connected to tubing 22 which may be connected by luer fitting 70 to tubing (not shown) leading from a source (not shown) of cardioplegic fluid, while the other branch 26 of hub 14 is connected to tubing 28 which may be connected by a press-fit connector 30 to the tubing (not shown) leading from a vacuum source (not shown). Tubing 22 is secured to the leading end of the luer fitting by means of an elastic band 73 placed over the tubing. Connector 30 can be a standard plastic coupler having ridges on the ends thereof to provide a secure, air-tight seal when inserted into the tubing 28.

The length of tubing 28 is selected such that it is long enough to easily be maneuvered for attachment to the tubing (not shown) connected to the vacuum source but is not so long as to be cumbersome while the cannula assembly 10 is being inserted into the aorta. Additionally, inasmuch as it is not always desirable to apply the vacuum to the interior of the aorta, a Halsey-Roberts clamp 32 is positioned on tubing 28. Clamp 32 can be used to securely occlude tubing 28, thus shutting off the suction. The Halsey-Roberts clamp 32 is especially adapted to this use because it remains on tube 28 when disengaged so that it cannot become misplaced, and it is easily operable with one hand.

Figure 3:
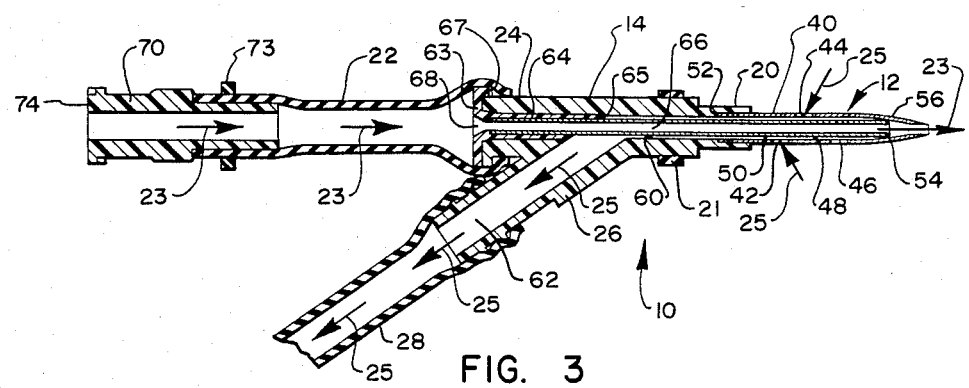
FIG. 3 is a longitudinal cross-sectional view of the cannula of FIG. 1, with the trocar removed.

A trocar 16 is initially positioned through tubing 22, hub 14 and outer cannula 40 to facilitate the insertion of needle portion 12 into the aorta. The tip 18 of trocar 16 is sharpened and extends past the end of outer cannula 40 so that it can easily pierce the wall of the aorta and provide an opening through which the outer cannula 40 of needle portion 12 can be inserted. Once the outer cannula 40 is fully inserted, trocar 16 can be withdrawn and removed from cannula assembly 10, as illustrated in FIG. 3. After trocar 16 is removed from cannula assembly 10, tubing 22 can be connected to a source (not shown) of cardioplegic fluid for injection into the heart.

A small elastic band 21 is positioned on hub 14 behind forward end 20. The band 21 provides a means for anchoring the hub 14 so that it can be tied to the tourniquet of a purse string suture, as more fully described below in reference to FIGS. 5 and 6. It will be appreciated that band 21 could also be formed as an integral portion of hub 14, or that a groove could be formed in place in band 21 to provide the necessary anchoring means.

Figure 2:
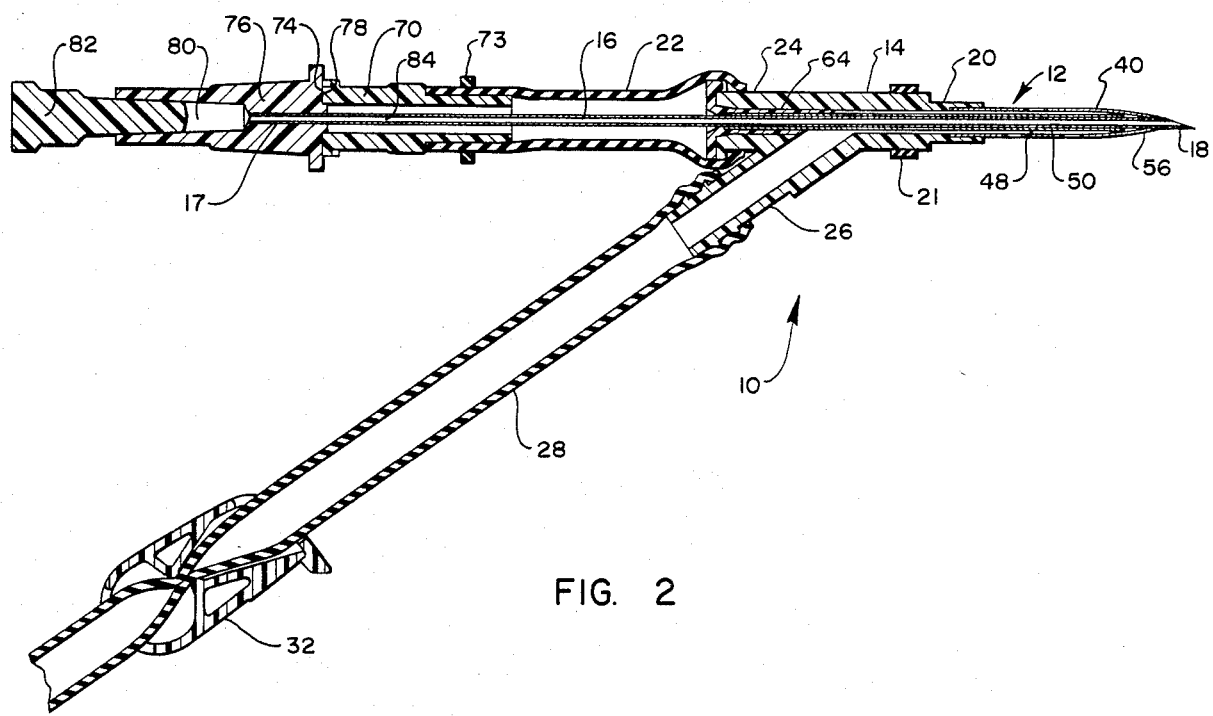
FIG. 2 is a longitudinal, cross-sectional view of the cannula of FIG. 1 taken along line 2—2.

Referring now to FIGS. 2 and 3, cannula assembly 10 of FIG. 1 is shown in greater detail in cross-section. FIG. 2 illustrates cannula assembly 10 with the trocar 16 in place and FIG. 3 illustrates the cannula assembly 10 with the trocar 16 removed.

With reference to FIG. 3, the outer cannula 40, which in the preferred embodiment is fashioned from Teflon TM, has holes 42, 44 and 46 (see Also FIG. 4) formed therein to allow air to be sucked into the outer lumen 48 which is defined by the space between outer cannula 40 and inner cannula 50. The placement of holes 42, 44 and 46 will be more fully discussed hereinafter with reference to FIG. 4.

With continued reference to FIG. 3, the trailing end of outer cannula 40 is anchored in recessed step 52 formed in the forward end 20 of hub 14. The leading end of outer cannula 40 extends past the leading tip 54 of inner cannula 50 and is tapered as at 56 to form a substantially fluid tight seal around tip 54. Thus, as further described below, air aspirated through holes 42, 44 and 46 will enter lumen 48 and will be evacuated from lumen 48 through the passageway 62 of branch 26 and tubing 28. The tapered leading end 56 also helps to provide a smooth surface for insertion of the needle portion 12 into the aorta. Tapered end 56 can be tapered by any suitable method such as by heating the outer Teflon TM cannula 40 and drawing it over a die.

As best illustrated in FIG. 3, inner cannula 50 extends through substantially the entire length of branch 24 of hub 14 and through outer cannula 40 up to about the midpoint of its tapered end 56. The trailing end of inner cannula 50 is anchored within a cylindrical plug 64 inserted in the end of branch 24 of hub 14.

Plug 24 is cylindrical in shape having a bore 68 passing through the center thereof. Plug 64 seals branch 24 so that the space between the outside diameter of inner cannula 50 and the inside diameter of branch 24 will not be open to fluids aspirated into lumen 48. The forward end 65 of plug 64 is beveled so as to conform to the angle formed by channel 62 of branch 26. Thus, any blood which is aspirated into lumen 48 will follow a smooth flow path into the passageway 62 of branch 26 and tubing 28, and will be less likely to clot or clog the passageway 62 or lumen 48. Abrupt corners and recesses are to be avoided because they would provide a site for the blood to coagulate and possibly occlude the lumen 48 or passageway 62.

The rearward portion of plug 64 is defined by a flat head 63 which abuts against the trailing end of branch 24 of hub 14. Head 63 has a small tab 67 formed on its inner surface which is aligned with a corresponding slot formed in the trailing end of branch 24. Tab 67 and the corresponding slot insure that plug 64 is correctly positioned such that the beveled forward end 65 of plug 64 is correctly aligned with the angle formed by passageway 62 of branch 26.

With continuing reference to FIG. 3, inner lumen 66 is defined by the bore 68 of plug 64, the lumen of inner cannula 50, and the forward portion of the lumen of outer cannula 40 at its tapered end 56. After the trocar 16 (see FIG. 2) is removed from the assembly as shown in FIG. 3, cardioplegic fluid is communicated through luer fitting 70 and tubing 22 to the inner lumen 66, from which it is injected into the aorta, as schematically represented by arrows 23. At the same time, air may be aspirated as schematically shown by arrows 25 through holes 42, 44 and 46 into outer lumen 48 which is sealed from inner lumen 66 at the tapered end 56 of cannula 40, and at the plug 64 positioned in branch 24. Thus, cardioplegic fluids may be injected in the direction of arrows 23 into the aorta, while air may be aspirated in the direction of arrows 25 through lumen 48 and passageway 62.

Referring now to FIG. 2, the positioning of trocar 16 within assembly 10 is illustrated. In the preferred embodiment trocar 16 comprises a hollow, stainless steel needle which extends from its forward tip 18 through inner cannula 50, plug 64, tubing 22, and luer fitting 70, where its trailing end 17 terminates in a hub 76 which has a female luer fitting 78 adapted to receive the male fitting of luer connector 70. The length of trocar 16 is selected such that its forward tip 18 extends just beyond the forward end 56 of cannula 40 when hub 76 is connected to fitting 70. A chamber 80 is formed in hub 76 and a plug 82 is normally placed within chamber 80 to seal the passageway 84 of the hollow needle.

Although trocar 16 has been illustrated as a hollow needle, it will be readily appreciated that it could also be formed as a solid piece. Its purpose is to provide some rigidity to assembly 10 while it is being inserted and to provide a sharped tip for piercing the aorta to provide a hole through which needle portion 12 can be inserted.

Figure 4:
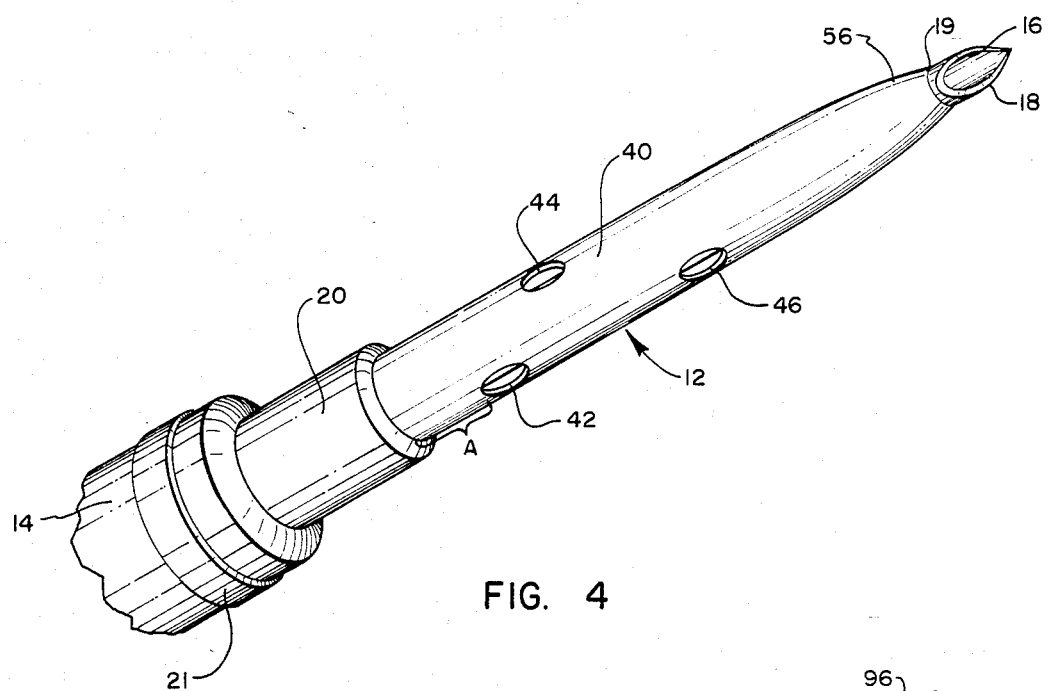
FIG. 4 is a perspective view of the tip portion of the cannula of FIG. 1 with the trocar in place.

Referring next to FIG. 4, the forward portion of assembly 10 is illustrated in an enlarged perspective view. Forward end 56 of outer cannula 40 is tapered as described above such that a generally smooth continuous outer surface is formed by trocar 16 and outer cannula 40 to facilitate insertion into the aorta. Holes 42, 44 and 46 are spirally positioned around the surface of outer cannula 40 to provide inlets for the aspirated air. In the preferred embodiment, holes 42 and 44 are circumferentially spaced 120° from each other. A fourth hole (not shown) is further spaced 120° from hole 44. Accordingly, hole 46 which is spaced 120° from the fourth hole is in alignment with hole 42. By placing the holes in this configuration it is possible to suck air from all sides of the cannula while maintaining sufficient structural rigidity of outer cannula 40.

Figure 6:
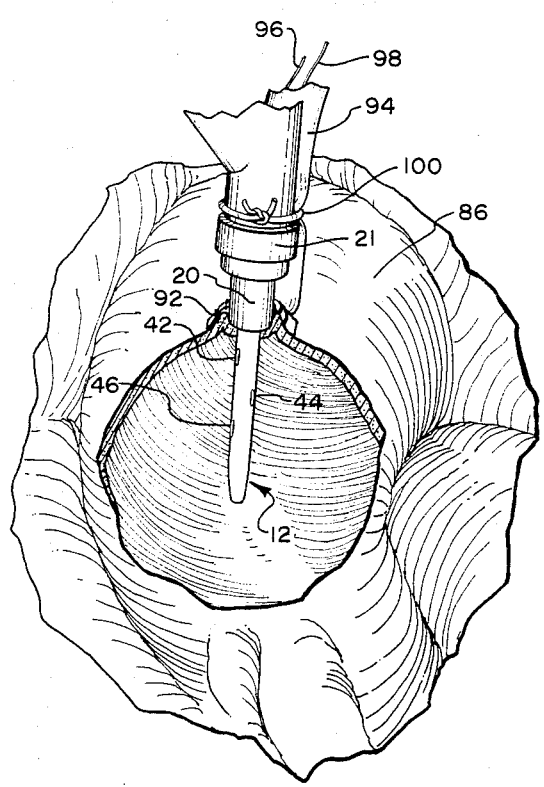
FIG. 6 is a partially broken away perspective view of an aorta illustrating the positioning of the cannula.

Hole 42 is spaced from forward end 20 of hub 14 by the distance "A", which is approximately ⅛ of an inch. This distance is equal to the average thickness of the aortic wall. Thus, when assembly 10 is positioned in the aorta with forward portion 20 abutting the aortic wall, hole 42 is positioned immediately below the inner surface of the aortic wall, as illustrated in FIG. 6. Holes 42, 44 and 46 are typically formed in outer cannula 40 by carefully drilling them to insure that the holes are formed with precision and without any ragged edges or debris attached to the holes.

Figure 5:
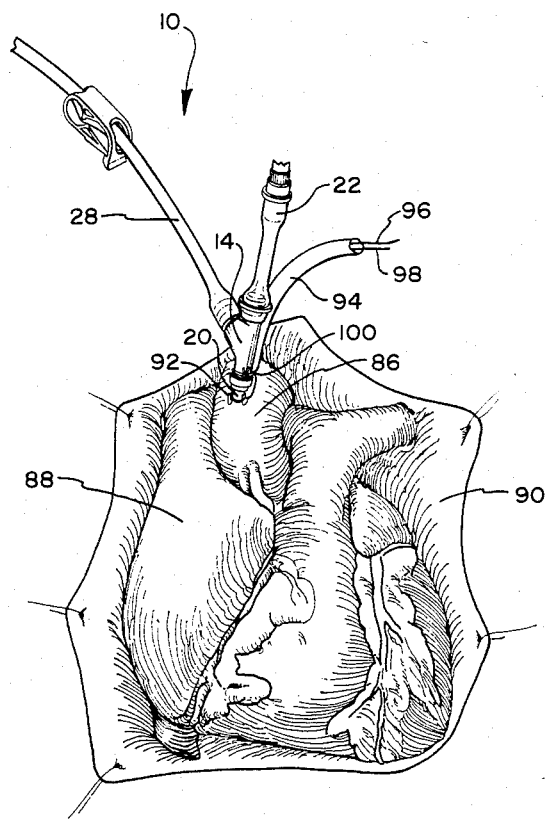
FIG. 5 is a perspective view of a heart with the cardioplegia/air aspiration cannula of the present invention positioned in the aorta.

Referring next to FIG. 5, assembly 10 is illustrated in position in an aorta 86 of heart 88. When the pericardium 90 is pulled away from the heart 88, the aorta 86 can easily be located at the top of the heart. A small "purse string" suture 92 is formed in the aorta. After the suture is formed, a tube 94 is positioned over the trailing ends 96 and 98 of the threads to act as a tourniquet for tightening the purse string suture.

Once the suture is formed and the tourniquet is in place, needle portion 12 can be inserted into the aorta through the area defined by the purse string suture. The sharpened tip 18 of trocar 16 (See FIG. 4) pierces the aortic wall and creates an opening through which outer cannula 40 can be inserted. Outer cannula 40 is inserted until the forward end 20 of hub 14 abuts the aortic wall, as shown in FIG. 6. The overall length of the needle portion 12 is such that when carefully inserted, the tip 18 of trocar 16 will not quite reach the opposite wall of the aorta, thus minimizing the possibility that the opposite wall will not be inadvertently punctured.

Purse string suture 92 is then tightened around the outer cannula 40 by pulling the ends 96 and 98 of the threads through tourniquet 94, which is, at the same time, pushed down to the aortic wall next to the forward end 20 of hub 14. Tourniquet 94 is then tied to hub 14 with a string 100. String 100 is fastened immediately above band 21 on hub 14, which prevents the string from sliding off the end of hub 14. After the hub 14 has been securely fastened to the tourniquet 94, tubing 28 can be attached to a vacuum source and tubing 22 can be attached to a source of cardioplegic fluid.

As illustrated best in FIG. 6, hole 42 is positioned immediately below the aortic wall. The other holes 44 and 46 are positioned at varying depths. Thus, air can be easily aspirated from the aorta at varying depths. After the operation on the heart is completed, string 100 can be cut and needle 12 can be withdrawn from the aorta. Purse string suture 92 can then be further tightened to seal the small puncture wound that was formed in the aortic wall.

As can be seen from the foregoing, the present invention provides a device for delivering cardioplegic fluid and for aspirating air which is effective and is simple to use. It is especially significant that the present invention can perform both functions through a single, small puncture in the aorta thus lessening the trauma to the aorta.

Additionally, because of the ease with which the present invention can be inserted and removed, the length of time required to perform the surgery is reduced thus lessening the length of time that the patient is on cardiopulmonary bypass and/or anesthesia.

It should be further appreciated that while the present invention has been particularly described in reference to the presently preferred embodiment, the invention may be embodied in other specific forms without departing from its spirit or essential characteristics. Thus, the described embodiment is to be considered in all respects only as illustrative and not restrictive. The scope of the invention is, therefore, indicated by the appended claims rather than by the foregoing description, and all modifications or changes which come within the meaning and range of equivalency of the claims are to be embraced within their scope.

What is claimed and desired to be secured by United States Letters Patent is:

1. An apparatus for delivering cardioplegic fluid to and for aspirating air from the aorta during cardiac surgery, said assembly comprising:

an inner cannula for forming a first lumen through which a cardioplegic fluid is delivered;

an outer flexible cannula for forming a second lumen through which air is aspirated, said outer cannula having at least one opening formed in the side thereof, said outer cannula having a substantially constant wall thickness and extending beyond the tip of said inner cannula, the forward end of said outer cannula being blunt and slightly tapered to sealing engage said tip of the inner cannula, such that the aspirated air and cardioplegic fluid will travel through said second and first lumens, respectively; and means for connecting said first lumen to a source of cardioplegic fluid and for connecting said second lumen to a vacuum source.

2. An apparatus as defined in claim 1 wherein said second lumen is formed in a concentric space between said inner and outer cannulae.

3. An apparatus as defined in claim 2 wherein said means for connecting said first lumen to a source of cardioplegic fluid and for connecting said second lumen to a vacuum source comprises a hub to which said inner and outer cannulae are concentrically mounted, said hub having a first branch defining a first flow path through which said cardioplegic fluid is delivered to said first lumen, and having a second branch angularly joined to said first branch and defining a second flow path through which said air is aspirated from said second lumen.

4. An apparatus as defined in claim 3 further comprising a plug for sealing a portion of the space between said inner and outer cannulae such that blood and air aspirated through said second lumen will pass through said second flow path defined by said branch, said plug comprising a beveled forward end adapted to conform to the angle formed by said angularly joined second branch, and means for aligning said plug relative to said hub so as to insure that said plug is correctly positioned with said beveled end in alignment with the angle formed by said second branch.

5. An apparatus as defined in claim 2 further comprising a removable trocar which extends through said first branch and said inner cannula, and which is long enough to permit the leading tip of said trocar to extend slightly beyond the end of said outer cannula to facilitate insertion of said cannula assembly into said aorta through a single puncture wound.

6. An apparatus as defined in claim 2 wherein said outer cannula has a plurality of openings formed in the side thereof, said openings being spaced one from the other in a spiral configuration about the exterior surface of said outer cannula.

7. A cannula assembly for delivering cardioplegic fluid to and for aspirating air from the aorta during cardiac surgery, said assembly comprising:
a hub;
an inner cannula mounted to said hub and having an inner lumen through which a cardioplegic fluid is delivered;
an outer flexible cannula mounted to said hub and through which said inner cannula is concentrically positioned so as to form an outer lumen in the space between said inner and outer cannulae, said outer cannula having a substantially constant wall thickness and extending beyond the tip of said inner cannula, the forward end of said outer cannula being tapered to sealing engage said tip of the inner cannula, and said outer cannula having at least one opening formed in the side thereof through which air is aspirated into said outer lumen; and
means for connecting said innner lumen to a source of cardioplegic fluid and for connecting said outer lumen to a vacuum source.

8. An assembly as defined in claim 7 wherein said means for connecting said inner lumen to a source of cardioplegic fluid and for connecting said outer lumen to a vacuum source comprises a first branch of said hub through which said inner cannula extends and through which said cardioplegic fluid is delivered to said inner lumen, and said hub having a second branch angularly joined to said first branch and through which blood and said air is aspirated from said outer lumen.

9. An apparatus as defined in claim 8 further comprising means for sealing said first branch from said second branch so that blood and said air aspirated from said outer lumen will flow from said outer lumen through said second branch of said hub.

10. The assembly of claim 9 wherein said means for sealing said first branch from said second branch comprises a generally cylindrically shaped plug positioned in the trailing end of said first branch of said hub, said plug sealing a portion of said outer lumen so as to prevent air aspirated from said outer lumen from entering said first branch, and said plug comprising a beveled forward end adapted to conform to the angle formed by said angularly joined second branch, and means for aligning said plug relative to said hub so as to insure that said plug is correctly positioned with said beveled end in alignment with the angle formed by said second branch.

11. An assembly as defined in claim 7 wherein said outer cannula further comprises a plurality of openings formed in the side thereof through which air is aspirated into said outer lumen, said openings being spaced about the outer surface of said outer cannula in a spiral configuration.

12. An assembly as defined in claim 7 further comprising a removable trocar which extends through said first branch and said inner cannula, and which is long enough to permit the leading tip of said trocar to extend slightly beyond the leading end of said outer cannula to facilitate insertion of said cannula assembly into said aorta through a single puncture wound.

13. A cannula assembly for delivering cardioplegic fluid to and for aspirating blood and air from the aorta during cardiac surgery, said assembly comprising:
an inner cannula having an inner lumen through which a cardioplegic fluid is delivered;
an outer flexible cannula concentrically spaced from said inner cannula so as to form an outer lumen in the space between said inner and outer cannulae, said outer cannula having a plurality of openings formed in the side thereof through which air is aspirated into said outer lumen, said outer cannula having a substantially constant wall thickness extending slightly beyond the leading end of said inner cannula and being blunt and slightly tapered to engage said leading end of the inner cannula so that said outer lumen is essentially sealed off from said inner lumen;
a hub to which said inner and outer cannulae are concentrically mounted, said hub having a first branch through which said cardioplegic fluid is delivered to said inner lumen, and having a second branch through which blood and air is aspirated from said outer lumen;
a plug for sealing that portion of the space between said inner and outer cannulae which extends through said first branch of said hub, said plug comprising a beveled forward end adapted to conform to the angle formed by said angularly joined second branch, and means for aligning said plug relative to said hub so as to insure that said plug is correctly positioned with said beveled end in alignment with the angle formed by said second branch; and a removable trocar which extends through said first branch and said inner cannula, and which is long enough to permit the leading tip of said trocar to extend slightly beyond the end of said outer cannula to facilitate insertion of said cannula assembly into said aorta through a single puncture wound.

* * * * *

UNITED STATES PATENT AND TRADEMARK OFFICE
CERTIFICATE OF CORRECTION

PATENT NO. : 4,531,935

DATED : July 30, 1985

INVENTOR(S) : RICHARD BERRYESSA

It is certified that error appears in the above-identified patent and that said Letters Patent is hereby corrected as shown below:

```
Column 1, line 62, "fibrilate" should be --to fibrillate--
Column 2, line 58, "diametrically" should be --diametrally--
Column 4, line 41, "Plug 24" should be --Plug 64--
Column 5, line 29, "sharped" should be --sharpened--
Column 7, line 1,  "sealing" should be --sealingly--
Column 7, line 59, "sealing" should be --sealingly--
Column 7, line 63, "innner" should be --inner--
```

Signed and Sealed this

Twelfth Day of November 1985

[SEAL]

Attest:

DONALD J. QUIGG

*Attesting Officer*     *Commissioner of Patents and Trademarks*